(12) United States Patent
Whittle et al.

(10) Patent No.: US 7,088,914 B2
(45) Date of Patent: Aug. 8, 2006

(54) DEVICE, METHOD AND RESISTIVE ELEMENT FOR VAPORIZING A MEDICAMENT

(75) Inventors: Brian Anthony Whittle, Hornsea (GB); John Erwin Richard Bowyer, Swindon (GB); Anthony Hamish Harper, Swindon (GB); Anthony Vanhinsberg, Swindon (GB); Christopher Robert Melbourne, Swindon (GB); David Downs, Salisbury (GB); Rajiv Bobby Dave, Edgware (GB)

(73) Assignees: GW Pharma Limited (GB); Tyco Electronics UK Limited (GB)

( * ) Notice: Subject to any disclaimer, the term of this patent is extended or adjusted under 35 U.S.C. 154(b) by 0 days.

(21) Appl. No.: 10/494,136

(22) PCT Filed: Oct. 31, 2002

(86) PCT No.: PCT/GB02/05007

§ 371 (c)(1),
(2), (4) Date: Nov. 12, 2004

(87) PCT Pub. No.: WO03/037412

PCT Pub. Date: May 8, 2003

(65) Prior Publication Data

US 2005/0063686 A1 Mar. 24, 2005

(30) Foreign Application Priority Data

Oct. 31, 2001 (GB) .................................. 0126150.2

(51) Int. Cl.
*A61M 16/00* (2006.01)
*H05B 3/00* (2006.01)

(52) U.S. Cl. .................. 392/390; 392/386; 128/203.27

(58) Field of Classification Search ................. 392/386, 392/387, 390, 394, 395; 128/202.21, 203.12, 128/203.16, 203.17, 203.26, 203.27; 219/490, 219/497, 504
See application file for complete search history.

(56) References Cited

U.S. PATENT DOCUMENTS

| 2,104,266 | A | | 1/1938 | McCormick |
| 3,789,190 | A | * | 1/1974 | Orosy et al. ................. 219/497 |
| 4,303,083 | A | | 12/1981 | Burruss, Jr. |
| 4,849,181 | A | | 7/1989 | Kelley et al. |
| 5,228,460 | A | | 7/1993 | Sprinkel et al. |

(Continued)

FOREIGN PATENT DOCUMENTS

DE 3701499 A1 1/1987

(Continued)

OTHER PUBLICATIONS

PCT International Search Report dated Jul. 3, 2003 for International Application No. PCT/GB 02/05007.

*Primary Examiner*—Sang Y. Paik
(74) *Attorney, Agent, or Firm*—Wolf, Greenfield & Sacks, P.C.

(57) ABSTRACT

A device for vaporizing a medicament (4). The device comprises a resistive element (9) on which the medicament is deposited. The device also comprises a source of electrical power which can be connected across the resistive element to vaporize the medicament. The element is configured to provide a central cool region (11) on which the medicament is deposited and a relatively hotter region (12) surrounding the cool region. Through holes (13) are also provided. The resistive element may be a mesh, foil or a tile on which a resistive pattern is deposited.

10 Claims, 4 Drawing Sheets

U.S. PATENT DOCUMENTS

| | | | |
|---|---|---|---|
| 5,708,256 A * | 1/1998 | Montagnino et al. | 219/497 |
| 5,825,975 A | 10/1998 | Privas | |
| 2003/0049025 A1 * | 3/2003 | Neumann et al. | 392/390 |

FOREIGN PATENT DOCUMENTS

| | | |
|---|---|---|
| DE | 4301912 A1 | 1/1993 |
| EP | 0 904 791 A2 | 3/1999 |
| EP | 0 911 041 A2 | 4/1999 |
| GB | 318214 A1 | 9/1930 |
| GB | 2 192 337 A1 | 1/1988 |
| GB | 2 332 844 A1 | 6/1999 |
| JP | 11156536 A1 | 12/1997 |
| WO | WO 92/19135 A1 | 11/1992 |
| WO | WO 94/09842 A1 | 5/1994 |
| WO | WO 97/02054 A1 | 1/1997 |
| WO | WO 98/59527 A1 | 12/1998 |
| WO | 01/50849 * | 7/2001 |

* cited by examiner

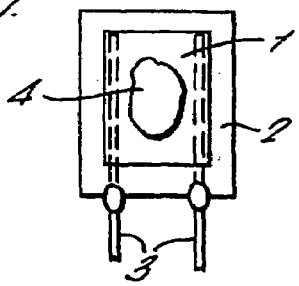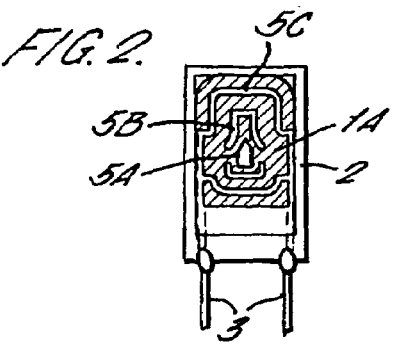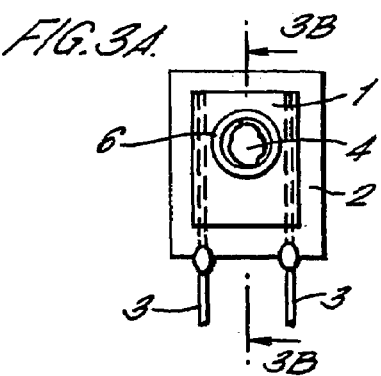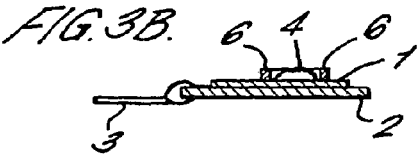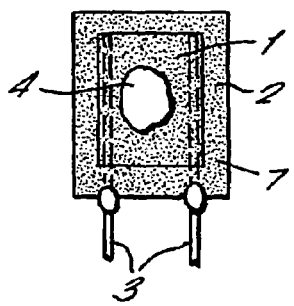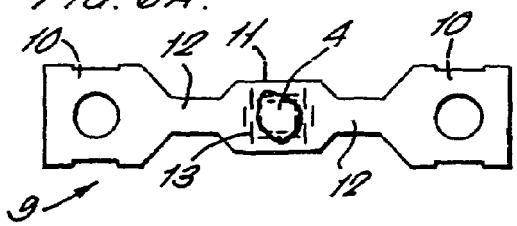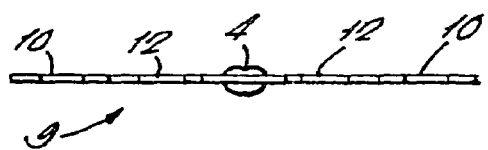

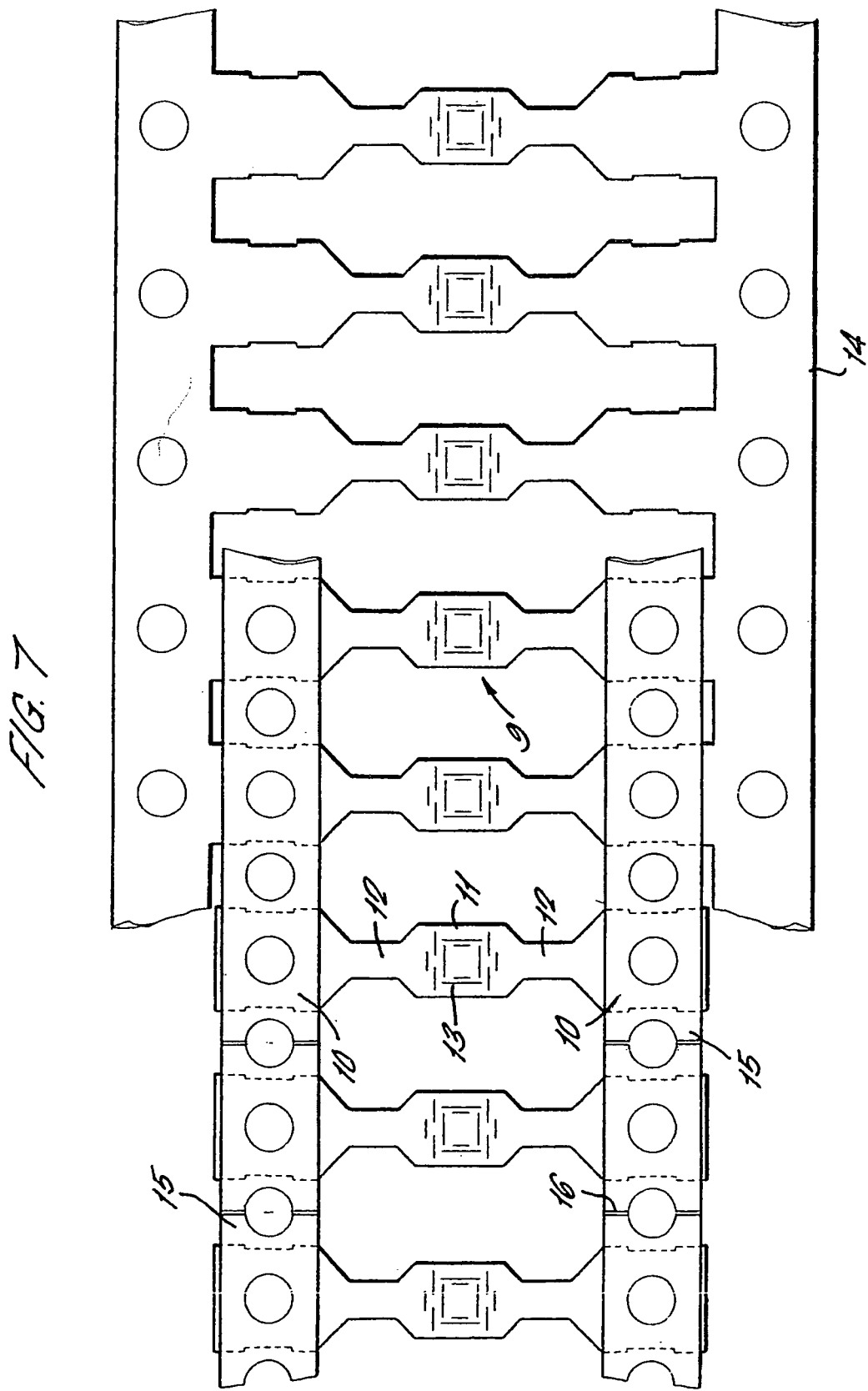

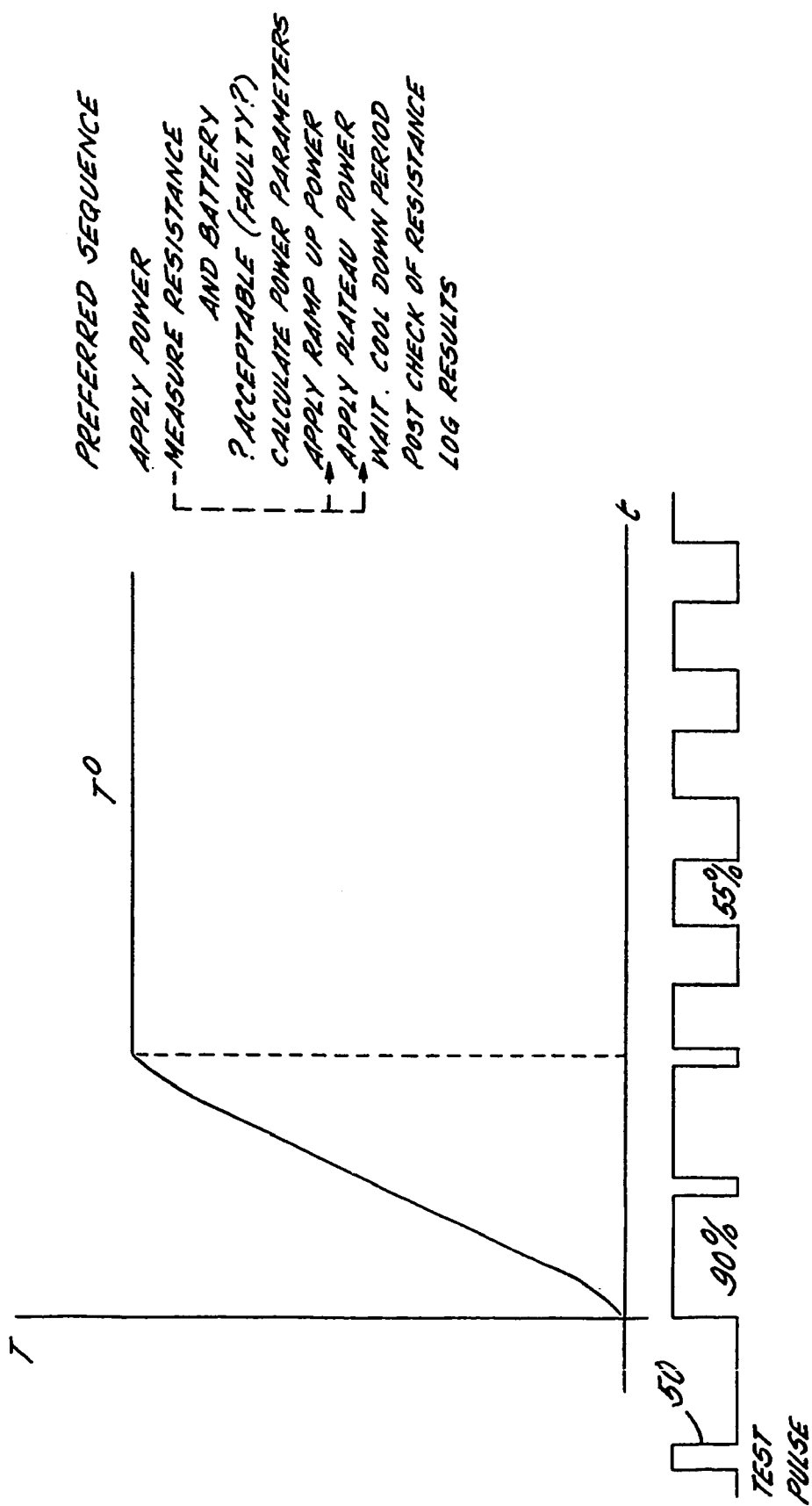

DEVICE, METHOD AND RESISTIVE ELEMENT FOR VAPORIZING A MEDICAMENT

RELATED APPLICATIONS

This application is a National Stage application of PCT International Application No. PCT/GB02/05007 filed, Oct. 31, 2002.

The present invention relates to a device, method and resistive element for vaporising a medicament, and in particular a cannabis extract.

The administration of medicaments via the respiratory tract is appropriate for certain types of medicaments. The advantages and limitations of this route are well recognised. Administration by the respiratory route is already used for anaesthetics and for substances which have a local effect on the respiratory tract. These include, but are not limited to bronchodilator (β-adranergic agonist and parasympathetic antagonist) drugs, anti-asthmatic and smooth muscle relaxant drugs. The administration of drugs of this type depends on formulation of the substance as a solution which is delivered as a fine aerosol, or as a cloud of fine particles.

A number of devices have been described which can be used to deliver medicaments either as aerosols or as fine particles and there are several advantages of this type of formulation. Drugs with a local action on the lining of the lungs have immediate access and act quickly. The medicament is given in the form of a suspension or mist and it is possible to control the area of the lung that is reached, by control of particle size. Lungs have a good blood supply and absorption in the systemic circulation is rapid. Medication absorbed by the lungs is quickly distributed by the heart and major blood vessels to organs such as the brain and skin without first passing through the liver. Drugs that are absorbed from the gastro-intestinal tract are taken into the hepatic portal system and in the liver a large proportion of the dose may be destroyed by the metabolic activity of the liver—the so called "first pass effect".

There are two main types of currently available device designed to produce a fine particle suspension for aerosols for administration of medication to the respiratory tract. These are dry particle inhalers which deliver a cloud of particles to the flow of air breathed in by the patient and metered dose inhalers which are aerosols which deliver the drug through a break-up valve to produce a fine spray. Neither device is particularly efficient as it does not allow accurate control of the particle size.

Within a defined particle range. Particles with a mean aerodynamic diameter of more than 15 microns have sufficient mass to hit the back of the throat, miss the respiratory tract and are swallowed. Swallowed medication is then subject to the first pass metabolic effect and because of their large size these particles may account for a large proportion of the dose delivered. Particles with a mean size of 5–15 microns tend to be deposited high up in the bronchial tree, from where they are not well absorbed. Particles with a size of 1–5 microns reach the level of the bronchi and have the greatest chance of being absorbed in the terminal bronchioles and exerting their pharmacological effect after absorption into the blood. Particles below about 1 micron mean diameter are within the size range where Brownian movement occurs and it is possible for very small particles to be breathed out again in the expired air.

Further, both of these types of inhaler devices rely on the production of a mist or cloud of particles which are not themselves volatile.

Delivery to the site of absorption of a fine particle suspension or aerosol is dependent on many factors which are difficult to standardise. On the other hand, the delivery of medication in the form of a vapour has been shown not to be subject to the same limitations.

There are a number of known ways of delivering a medicament in vaporised form.

Devices for the administration of anaesthetic gases are well described. Devices for the administration of essential oils consist of an absorbent matrix which is impregnated with the essential oil. Where the medicament has a significant vapour pressure at ambient room temperature, drawing air through the impregnated matrix releases a charge of medicament into the inspired air. This type of device is not suitable where the medicament has a low vapour pressure at ambient room temperature.

Smoking is another means of delivering a vaporised medicament. However, this involves well known health risks. Further, some of the medicament is burnt to provide heat.

A device specifically designed for the vaporisation of a crude natural product is disclosed WO 99/11311. This discloses the vaporisation of a crude natural product or other volatile substance impregnated into an inert matrix by forcing a stream of hot air through the substance. Although such a device is more effective than cigarette smoking as it avoids pyrolysis of the substance, there are a number of drawbacks with this approach. For example, it is not able to deliver an accurately metered dose. Further, as the apparatus requires a heater and a fan it is bulky. In essence, this device does not lend itself to domestic use by a patient to deliver a regular and controlled supply of the medicament.

WO 94/09842 discloses a drug vaporiser which uses an electrically conductive material through which a current is passed to provide a resistive heater to vaporise the drug. A number of advantages arise from such an arrangement.

In particular arrangement allows the temperature and time of vaporisation to be closely controlled thereby avoiding pyrolysis of the medicament. Further, the dosage of the medicament is readily controllable as it is determined by the amount of medicament coated on the resistive element. The use of the electrical power supply alone to vaporise the medicament results in a device which is considerably more compact than that disclosed in WO 99/11311. Also, vaporisation can be done at the time of use so that a medicament can be stored without untoward degradation before use at room temperature.

However, there are considerable practical difficulties with the device of WO 94/09842. The main problem is that the centre of the resistive element becomes hotter than a region closer to the periphery. This causes the molten substance which has not yet vaporised to flow almost instantaneously towards the cooler part of the resistive element, which generates a flow of the substance towards the edge of the resistive element such that it quickly flows off the element. This severely limits the amount of medicament which can be vaporised.

Therefore, according to a first aspect of the present invention, there is provided a device for vaporisation of a medicament, the device comprising a resistive element on which the medicament is deposited; a source of electrical power; a connector to connect the source of electrical power across the resistive element; and a controller to control the supply of power to the resistive element to vaporise the medicament; wherein the resistive element is configured to produce, in use, a relatively cool central region on which the substance is deposited and a relatively hot region at least partially surrounding the cool region.

This creates a positive thermal differential, effectively reversing the problems encountered with a uniform resistor. This tends to deter the medicament from flowing across the hot region thereby holding it in a "pool" at the central region.

The object is to achieve a significant temperature gradient which will vary depending on the material. In one example, there is 10–20° C. difference between the cool central region and the surrounding relatively hot region.

It should be noted that the term "medicament" covers a substance which gives rise to a medicament on vaporisation.

The resistive element may be a thick film resistor on a substrate, but the current preference is for a mesh or foil resistive element as these consume less power and hence are well suited to units which are powered by commercially available rechargeable batteries, such as those used in mobile phones. The mesh may be a ribbon mesh or a fused mesh which is essentially a hybrid between a mesh and a foil.

When the resistive element is a thick film resistor, this cool/hot differential is accomplished by selectively screen printing the resistive material or selectively removing resistive material from the central region of the resistive element. In the case of a mesh or foil, this is accomplished by providing at least one constricted region away from the central portion which generate a higher current density away from the central portion hence preferentially heating the constricted regions.

In the current preferred embodiment, when the resistive element is a foil or mesh it is provided with a respective constricted region between the substance and each contact point. This generates a central portion on which the substance is deposited. This central portion is flanked on one or more sides by the constricted regions which become preferentially heated once the current is supplied to create a thermal barrier deterring flow of the substance away from the central portion.

If the element is a mesh it may be similarly shaped. However, preferably the mesh is sized with respect to the deposited medicament so that, in use, the thermal mass of the medicament is sufficient to produce the relatively cool central region.

This has the same effect as shaping the resistor in the manner mentioned above.

More particularly, the size of the mesh can be made small enough and the spacing between adjacent mesh elements large enough that the thermal mass of the mesh in the vicinity of the deposited medicament is preferably substantially equal to or less than the thermal capacity of the medicament.

The first aspect of the present invention also extends to a resistive element having a medicament deposited thereon and having contact points which connect, in use, with an electrical power supply; wherein the resistive element is configured to produce, in use, a relatively cool central region on which the substance is deposited and a relatively hot region at least partially surrounding the cool region. This forms an independent aspect of the invention in its own right, and also provides a resistive element suitable for use in a device referred to above.

According to a second aspect of the present invention there is provided a device for vaporisation of a medicament, the device comprising a resistive element on which the medicament is deposited; a source of electrical power; a connector to connect the source of electrical power across the resistive element; and a controller to control the supply of power to the resistive element to vaporise the medicament; wherein the element is provided with a number of surface inconsistencies to provide keying for the deposited medicament.

The surface inconsistencies provide keying for the medicament, and nucleation sites for the medicament and also generally increase the surface area of the element. The inconsistencies may, in particular, be apertures or may be provided by a roughened surface.

The apertures allow the medicament deposited on the resistive element to penetrate through the resistive elements so that it is effectively deposited on both sides of the element. This provides a larger surface area contact between the medicament and the resistive element thereby facilitating vaporisation. In effect, this increases the quantity of substance which can be vaporised.

For a mesh, of course, the apertures are inherently present. Foils, on the other hand, can be provided with a number of through apertures. These through apertures are preferably in the form of slits and are designed to mimic the action of the mesh, in that they allow the medicament to penetrate to the opposite side of the foil.

A further benefit with providing apertures in the foil or mesh is that they can be positioned to provide a tortuous path for the current passing through the element to the central region of the element. This can then produce a relatively cool region at the centre of the element providing the positive thermal gradient effect referred to above and enhancing the effect of constricted regions.

The second aspect of the present invention also extends to a resistive element having a medicament deposited thereon and having contact points which connect, in use, with an electrical supply; wherein the resistive element is provided with a number of surface inconsistencies to provide keying for the deposited medicament. This forms an independent aspect of the invention in its own right and also provides a resistive element suitable for use in a device referred above.

It will also be appreciated that the first and second aspects of the present invention may be combined.

Preferably, the medicament is for use in treating diseases of the respiratory tract, or one which is administered to avoid the first pass effect, such as a cannabis extract. The medicament is preferably an active medicament, but may also be an inactive medicament, which is only converted to an active medicament during the act of volatilisation, or is converted to a precursor which is only converted to an active form in the body. Indeed, in the case of cannabis extract, it is possible that the medicament deposited will be the inactive acid, volatilisation resulting in the decarboxylation and conversion to the active form.

Preferably, between 0.1 and 10 mg, and more preferably between 0.1 and 1 mg of cannabis extract is deposited on the resistive element. The extract may be a natural or synthetic cannabinoid such as THC, THCV, or CBD. Typically 95% of the extract is vaporised.

The device may be a single use device. However, for convenience, the device preferably comprises a plurality of resistive elements on each of which the medicament is deposited, and the device further comprises means to selectively vaporise the medicament on each element. The elements may be provided with pre-existing connections, and the controller may contain switching circuitry to select the element to be fired. Alternatively, means may be provided to bring the connector selectively into engagement with each of the resistive elements. This can either be done by providing a strip of resistive elements which are fixed within the device and making the connector movable between the elements.

However, a simpler and more compact arrangement is provided by using a means to advance the plurality of resistive elements selectively past a location where they can be brought into engagement with the connector. In this case, the resistive elements are preferably supplied on a replaceable unit, such as a wheel, drum or cassette. The cassette may have a first reel from which the elements are selectively advanced and a second reel on which spent elements are stored.

When the device is arranged to vaporise a medicament, it preferably also comprises a chamber into which the medicament is vaporised, and a mouthpiece communicating with the chamber allowing a user to inhale the vapour from the chamber. The vapour generated is substantially free of dust. In order to contain the vapour until suction occurs, a one-way valve preferably separates the chamber and the mouthpiece.

The device also lends itself readily to being provided with security mechanisms to prevent use either by an unauthorised user, or by an authorised user obtaining doses more frequently than the desired dosage regime.

The device is also preferably provided with a data port enabling information regarding the delivered dosage to be downloaded or uploaded from the device to facilitate monitoring by medical staff.

The security and monitoring aspects of the invention are dealt with in greater detail in our earlier co-pending application GB 0025809.5.

As an alternative to or in addition to the provision of a thermal gradient to contain the substance in its molten state on the resistive element, a physical barrier may be provided. In the case of the thick film resistor, this may take the form of a ring of material bonded to the surface of the resistor to surround the substance. In the case of the foil, a physical barrier may be provided by bending the sides of the foil out of the plane of the foil.

The structure of the resistive element described above in accordance with the first and second aspects of the present invention is able to maximise the amount of medicament that the device is capable of vaporising. However, it is also useful to control the device such that the medicament is transformed from its original form into a vapour as quickly as possible.

Any of the resistive elements may be provided with a coating of inert, organic or inorganic material so as to avoid degeneration or decomposition of the medicament.

According to a further aspect of the present invention there is provided a method for vaporising a medicament deposited on a resistive element, the method comprising connecting the resistive element to an electrical power supply and controlling the supply of electrical power to the resistive element to vaporise the medicament by varying the duty cycle of the power supply to ensure that the resistive element reaches a target temperature, and then reducing the duty cycle to maintain the target temperature for sufficient time to vaporise the medicament.

This provides a method of controlling temperature of the resistive element so that the target temperature is reached as quickly as possible and is subsequently maintained.

The method preferably further comprises controlling the power to vaporise the substance without pyrolysis.

When a number of resistive elements are provided, the method preferably further comprises selectively vaporising the substance of the resistive elements in turn, for example, by progressively moving the resistive elements into a vaporising position and connecting the source of electrical power to the resistive element in the vaporising position.

The controlling step also preferably comprises measuring the resistance once the resistive element is connected to the source of electrical power and adjusting the duty cycle of the power supply to compensate for variations in the measured resistance.

Examples of resistive elements and devices will now be described with reference to the accompanying drawings, in which:

FIG. 1 is a plan view of a first resistive element shown for background interest only;

FIG. 2 is a plan view of a second resistive element which is in accordance with the first aspect of the invention;

FIG. 3A is a plan view of a third resistive element shown for background interest only;

FIG. 3B is a cross-section through line 3B—3B in FIG. 3A;

FIG. 4 is a plan view of a fourth resistive element in accordance with the second aspect of the invention;

FIG. 5A is a plan view of a fifth resistive element which is in accordance with the first and second aspects of the invention;

FIG. 5B is a side view of the fifth resistive element;

FIG. 6A is a plan view of a sixth resistive element which is in accordance with the first and second aspects of the invention;

FIG. 6B is a side view of a sixth resistive element;

FIG. 7 is a plan view showing a strip of sixth resistive elements;

FIG. 10 is a graph of temperature against time of a heating profile applied to a resistive element.

Figure 8:
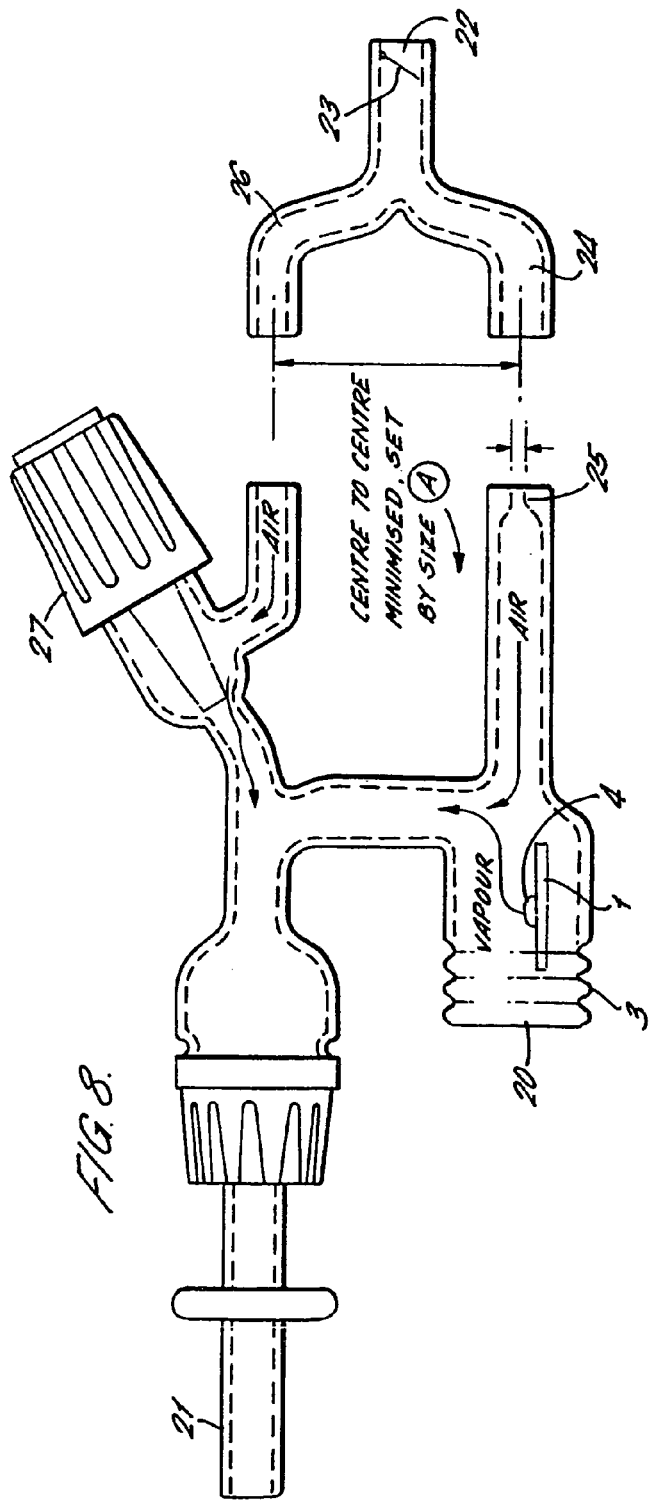
FIG. 8 is a schematic view showing the test rig for use in clinical trials.

The resistive elements set out in FIGS. 1 to 6 essentially shows the development history of the resistive element.

The first resistive element shown in FIG. 1 comprises a tile with a thick film rectangular ceramic resistor 1 which is either printed or deposited onto a substrate 2 in a manner well known in the art. A pair of connectors 3 are connected to the resistor 1 again in a known manner. The resistor is coated with a lead-free glaze and is then fired. A small amount of substance 4 is then deposited onto the resistor 1 in a manner to be described.

It was found that the temperature at the centre of the resistor became hotter than the surrounding portion of the resistor creating a thermal gradient which tended to cause the molten product to quickly run off the resistor. Thus, the arrangement of FIG. 1 is limited by its ability to retain a substance.

A second resistive element designed to overcome this problem is shown in FIG. 2. This arrangement is a tile generally the same as that shown in FIG. 1, and like references have been used to designate the same components. In this case, the resistor 1A has been laser ablated to have the shape as shown but the resistor may also be formed in a given shape e.g. by screen printing. For clarity, no substance is shown in FIG. 2, but this will be positioned similarly to that shown in FIG. 1. The pattern of laser ablation has removed the central portion 5A of the resistor 1A, as well as producing an inner incomplete ring 5B and an outer incomplete ring 5C. The effect of this is to create a cooler region towards the centre of the resistor, and a hotter portion outside this. As the molten substance tends to flow from a hot region to a cold region, this arrangement tends to cause it to pool towards the centre of the resistor. Thus, the second heating element is able to successfully vaporise a greater quantity of substance than the first heating element.

In order to provide an arrangement suitable for use by a patient in an unsupervised environment, a resistive element is required which can work satisfactorily even when the resistive element is at a considerable angle to the horizontal.

One element designed to operate under such conditions is shown in FIGS. 3A and 3B. This tile of similar construction to that shown in FIG. 1. The only difference is that the third arrangement has a ceramic ring 6 which surrounds the substance 4. The ceramic ring is placed on top of the glaze before the resistor is fired. The glaze fuses into the ring holding it in place. The ring 6 not only provides physical containment of the molten substance, but also acts as a cool mass which attracts the molten active substrate. It will be appreciated that the second and third resistive elements can be combined so that the laser ablated resistor shape is used in conjunction with the ceramic ring. Glass may be passivated over the ceramic ring to inhibit degradation of the medicament.

A fourth element is shown in FIG. 4. This is again similar to FIG. 1, but is covered with a particulate substance 7. This, may, for example, be sand, green ceramic, or Fullers earth. These are applied to the resistor with a screen and doctor blade on top of the layer of glaze before the resistor is fired. This creates a much larger surface area which makes vaporisation of the substance and inhibits run-off of the substance even when the resistor is tilted to the vertical. Again, the principle of this element may be combined with the previous or subsequent elements to provide further containment of the substance.

As an alternative to the particulate substance, a fibrous substance, such as glass fibre can be used. This provides the same benefit as the particulate matter.

One problem with this approach is that the particulate or fibrous substance could be dislodged from the resistor and become entrained in the vaporised substance.

A somewhat different approach is the fifth element shown in FIGS. 5A and 5B. The element is a mesh 8, for example of stainless steel and having 28μ wires and 36μ apertures. This provides significant advantages over the tiles previously referred to in that it provides a vast increase in the surface area of contact between the substance and the element. Further, the holes in the mesh allow the deposited substance to penetrate to the opposite side of the mesh 8. Thus, the mesh 8 of the fifth element essentially acts as a double sided element, while the tiles are only single sided. This provides considerably benefits to the speed of evaporation, and hence the amount of substance which can be vaporised. As well as providing a high surface area, the voids of the mesh also allow the surface tension of the drug to hold itself from either side of the mesh. The larger surface area of the mesh presents a number of nucleation sites improving vaporisation and reducing the possibilities of the molten substance running off of the element. Also, while the first two fourth resistive elements have a typical power demand of 16 watts, the typical power requirement for the fifth element is an order of magnitude lower typically at 2 watts. The mesh may be sintered or welded to prevent loose fragments from being drawn away in the airstream. Although the mesh element is shown with its wires arranged at an angle across the width of the mesh, benefits have been found if one set of wires extends in the longitudinal direction (i.e. left to right in FIG. 5A) while the other set extend across these in a generally transverse direction. Each wire may have a single strand or multiple strands.

A sixth embodiment is a foil element 9 as shown in FIGS. 6A and 6B. The currently preferred foil is 316 stainless steel. Other stainless steel may also be appropriate as is nichrome, aluminium or non-conductive film doped with a conductor or semi-conductor (e.g. silicon or graphite). The foil has a similar power requirement to the mesh 8.

Electrical connectors will be applied to the opposite ends 10 of the foil such that the current passes along the foil. Between the ends 10 and a central portion 11 of the strip where the substance 4 is positioned are a pair of constrictions 12. This reduction in surface area causes the constrictions 12 to heat up to a greater extent than the central portion 11 when the current is applied. These effectively operate as a barrier preventing the molten substance from spreading away from the central portion 11.

As shown in FIG. 6A, a pattern of through slits 13 is provided in the central portion 11. These fulfil a number of roles. Firstly, they allow the deposited substance to penetrate to the opposite side of the foil 9 as shown in FIG. 6B, and also provide keying for the substance. Also, they provide nucleation sites for the molten substance thereby promoting vaporisation. Finally, the particular configuration of slots shown provides a tortuous paths for the current to the middle of the central portion 11. This provides an additional differential heating effect to that provided by the constrictions 12 and ensures that the middle of the central portion 11 is colder than the outside of the central portion 11 which inhibits flow of the molten substance away from the middle of the central region 11.

FIG. 7 demonstrates how a number of the sixth elements are packaged suitable for use in a commercial product. A number of foil elements 9 are stamped from a long strip of foil such that they are connected by a bandolier 14. The through slits 13 are formed by laser machining. A plastic carrier 15 is then attached to the opposite ends 10 of the foil elements 9 before the bandolier 14 is cropped. The plastic carrier 15 may be provided with hinges 16 between the elements 9, allowing the carriers to be wound onto a reel, or allowing opposite ends of each carrier is to be joined to form a drum. If the elements are wound onto a reel, the plastic hinges will ensure that adjacent windings in the reel are held away from one another such that the substance on one element is not dislodged by contact with an adjacent element.

As an alternative to a reel or drum structure, the elements may be arranged in a wheel configuration with the elements running radially essentially forming the "spokes" of the wheel.

A first example of a device for dispensing the medicament will now be described with reference to FIG. 8. This apparatus is designed for clinical trials to be used in supervised circumstances to test the concept of vaporising a medicament using a resistive element.

The apparatus is made of borosilicate glass. A resistive element 1 carrying a substance 4 is provided in the lower left hand branch of the apparatus. This resistive element 1 is one of the tiles as shown in FIGS. 1 to 4.

An electrical contact is inserted through a port defined by a screw thread 20 and connected to contacts 3. For the clinical trials, the power supply is mains operated. Once this contact is in place, a sleeve (not shown) is screwed over the screw thread 20 to provide a seal. A mouthpiece 21 is provided as the top left hand branch of the apparatus and an air inlet 22 with a one-way valve 23 is provided on the opposite side of the apparatus. The air inlet stream then splits into a first stream medicament which flows through a restricted orifice 25 and mixes with the vapour from the resistor 1. A second stream 26 flows via a rotatable tap valve 27 and mixes with the combined vapour/air stream downstream of the initial mixing. The tap valve 27 allows users to vary the air/vapour ratio and determine an optimum value for this ratio.

The user inserts the mouthpiece 21 into his/her mouth. At this point, a negative pressure induced by sucking triggers the supply of current to the resistor 4 in a manner to be described to vaporise the substance. As the user sucks, the vapour is drawn up through the mouthpiece after mixing with air from the first stream 25 and a controlled amount of air from the second stream 26.

Figure 9:
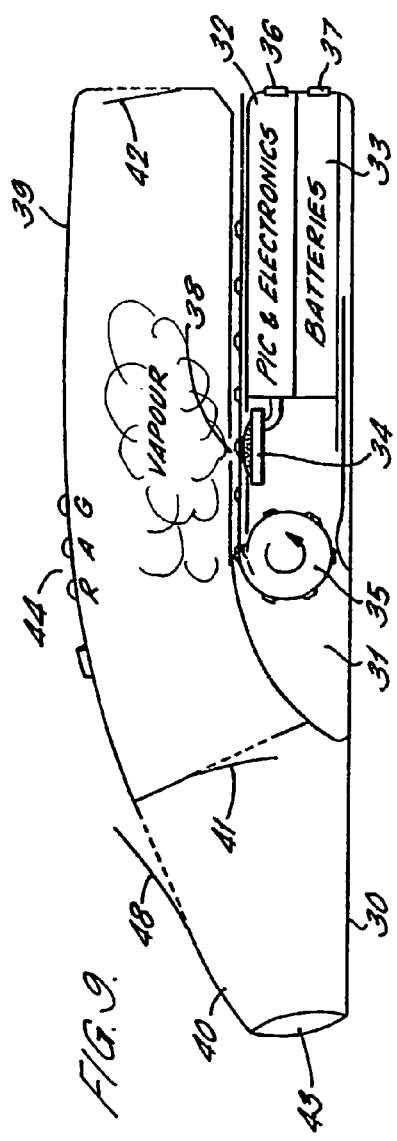
FIG. 9 is a schematic view of a device suitable for commercial use.

A device suitable for commercial use is shown in FIG. 9. This device is intended to be a hand-held device for home use. The device comprises a housing 30 having a first chamber 31 containing an electrical control circuit 32, one or more batteries 33 (a capacitor (not shown) may be provided to increase the maximum current available beyond that available from the battery alone), a pair of electrical connectors 34 (only one of which is shown in FIG. 9) and a spool 35 on which a line of resistive elements such as that illustrated in FIG. 7 is advanced over the electrical contacts 34. Although not shown in FIG. 9, it is intended that the line of elements 9 will be housed in a cassette having a first reel from which they are progressively unwound past a window in the cassette where they make contact with the electrical connectors 34, and onto a second reel where the spent elements are stored. Alternatively, a strip, or the drum or wheel arrangement mentioned above may be used. A communications port 36 is provided in communication with the controller 32 to allow information to be downloaded or uploaded from the controller. A recharging port 37 is provided to allow the battery to be recharged.

When a resistive element is in position to be contacted by the connectors 34, it is in registration with an aperture 38 opening into second chamber 39, such that when the electrical power is applied to the resistive element, the substance is vaporised into the second chamber 39. A second chamber 39 leads into a discharge chamber 40 via a one-way flap valve 41. A second one-way flap valve 42 is provided at the opposite end of the second chamber 39. Mouthpiece 43 provides an outlet from the discharge chamber 40.

The user inserts his/her mouth over the mouthpiece 43 and inhales. This draws air in through the one-way valve 42. This triggers the vaporisation of the substance as described below. The air together with the vapour are sucked through one-way valve 41 into the discharge chamber 40 and out of the mouthpiece 43. The amount of vapour generated is designed to be generated and inhaled during a single inspiratory cycle. Alternatively, only some of the substance may be vaporised, leaving some of the substance to be vaporised in one or more subsequent cycles. Also, if the substance contains a mixture of relatively low and relatively high boiling point constituents, only the relatively low point boiling point constituents may be vaporised leaving the relatively high boiling point constituents which can be vaporised in one or more subsequent cycles, or may remain on the element. Should the user, at any time blow into the mouthpiece 43, the expired air is vented from the discharge chamber 40 through a further one-way flap valve 48.

The quantum of heat used in vaporisation and the quantity of air with which the vapour is mixed is such that the respiratory tract is not scorched. Provision may be made for inducing a swirling motion in the volume of inhaled air so that the highest concentration of cannabinoid vapour is at the centre of the column of air. The periphery of the column contains a lower concentration, and it is this peripheral air which first meets the respiratory mucosa. Further, baffles may be introduced to give a uniform dilution of the concentrated vapour to produce a lower concentration of the inspired air.

The energy supplied to the resistive element is illustrated schematically in FIG. 10 showing temperature against time for a typical heating profile of the resistive element. A typical duty cycle is shown beneath the graph. Once the electrical contacts are brought into engagement with the resistive element, the test pulse 50 is initially emitted. From this, the impedance of the circuit is measured and the power parameters are determined accordingly. For example, if electrical resistance is below an accepted normal level, the power supplied to the resistive element will be increased. The initial requirement is for the resistive element to be brought up to the target temperature $T^o$ as soon as possible. To do this, the duty cycle is initially high (for example around 90%). Once the target temperature is reached the duty cycle is reduced (for example around 55%) to maintain the target temperature $T^o$ for a predetermined period of time sufficient to vaporise the substance. After a cool-down period a further test pulse is applied to provide a further check of the resistance across the resistor element. The test pulses are logged in the system controller and a fault is indicated should persistent unusual results be detected.

In order to dispense the substance, such as cannabis extract, on an industrial scale, the present intention is to use a piston driven dispenser similar to that used to deposit small quantities of adhesive onto small components. Such a dispenser dispenses a controlled volume of material which is monitored by a camera. In order to do this, the extracts must have a constant viscosity. This can be done by adding a solvent such as ethanol to the extract which is then removed by evaporation. However, the current preference is to control the temperature of the extract to maintain a constant viscosity.

The power applied to the resistor and the duty cycles during heating and maintenance will vary with factors such as heater type, type of substance, amount of substance, air flow and power source.

An example of the preparation of a cannabis extract for use on the resistive element is described below:

Plants are grown as clones from germinated seed, under glass at a temperature of 25° C.±1.5° C. for 3 weeks in medicament hour daylight; this keeps the plants in a vegetative state. Flowering is induced by exposure to 12 hour day length for 8–9 weeks.

No artificial pesticides, herbicides, insecticides or fumigants are used. Plants are grown organically, with biological control of insect pests.

The essential steps in production from seed accession to dried Medicinal Cannabis are summarised as follows:

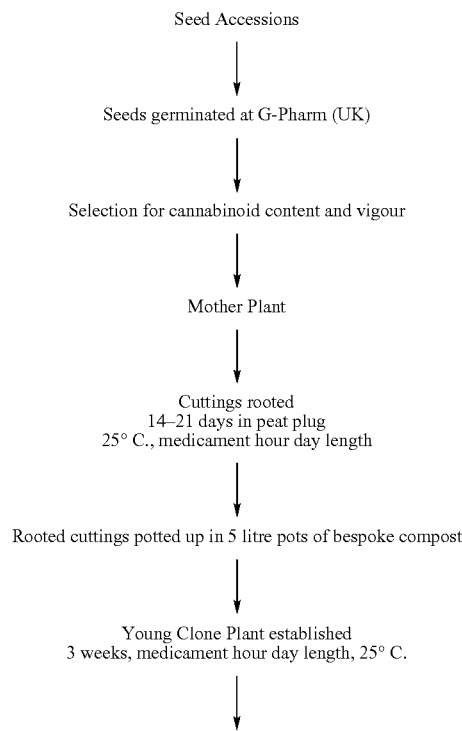

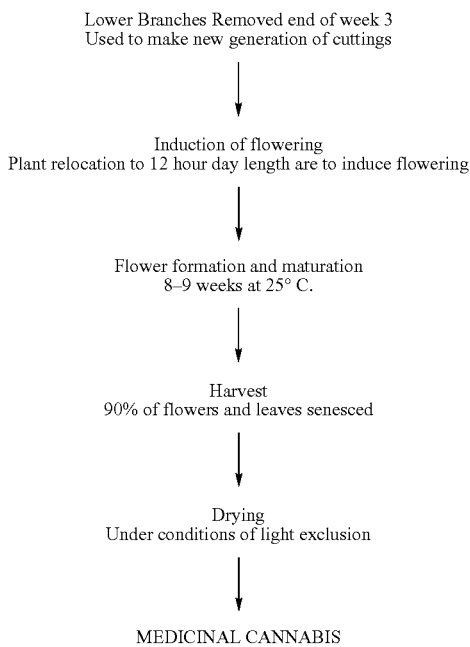

-continued
Lower Branches Removed end of week 3
Used to make new generation of cuttings Induction of flowering
Plant relocation to 12 hour day length are to induce flowering Flower formation and maturation
8–9 weeks at 25° C.

Harvest
90% of flowers and leaves senesced

Drying
Under conditions of light exclusion

MEDICINAL CANNABIS

The extract is then formed as follows:

A flow chart showing a process which can be used for manufacture of extracts from High-THC and High-CBD cannabis chemovars is given below:

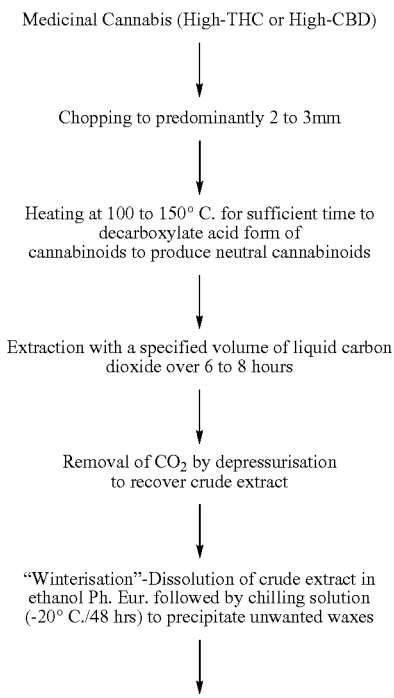

Medicinal Cannabis (High-THC or High-CBD)

Chopping to predominantly 2 to 3mm

Heating at 100 to 150° C. for sufficient time to decarboxylate acid form of cannabinoids to produce neutral cannabinoids Extraction with a specified volume of liquid carbon dioxide over 6 to 8 hours Removal of $CO_2$ by depressurisation to recover crude extract "Winterisation"-Dissolution of crude extract in ethanol Ph. Eur. followed by chilling solution (-20° C./48 hrs) to precipitate unwanted waxes -continued
Removal of unwanted waxy material by cold filtration Removal of ethanol from the filtrate by thin film evaporation under reduced pressure The step of heating at 100 to 150° C. for sufficient time to decarboxylate acid form of cannabinoids to produce neutral cannabinoids may be omitted, since cannabis medicinal extracts wherein the majority of cannabinoids are present in the inactive acid form may be administered directly as a vapour using the method of the invention. Decarboxylation and vaporisation to produce a therapeutic vapour comprising the free cannabinoids may be accomplished in a single vaporisation step.

The invention claimed is:

1. A method for vaporising a substance positioned in thermal communication with a resistive element, the method comprising connecting the resistive element to an electrical power supply and controlling the supply of electrical power to the resistive element to vaporize the substance by varying the duty cycle of the power supply to ensure that the resistive element reaches a target temperature, and then reducing the duty cycle to maintain the target temperature for sufficient time to vaporise the substance, and wherein the resistive element is configured to produce, in use, a relatively cool central region and a relatively hot region at least partially surrounding the cool region.

2. A method according to claim 1, further comprising controlling the power to vaporise the substance without pyrolysis.

3. A method according to claim 1, wherein there are a plurality of resistive elements, the method further comprising selectively vaporizing the substance on the resistive elements in turn.

4. A method according to claim 3, wherein the selectively vaporising step comprises progressively moving at least one of the resistive elements into a vaporising position and connecting the electrical power supply to the resistive element in the vaporising position.

5. A method according to claim 1, further comprising measuring the resistance once the resistive element is connected to the electrical power supply and adjusting the duty cycle of the power supply to compensate for variations in the measured resistance.

6. A method according to claim 1, wherein the substance is vaporised in one inspiratory cycle.

7. A method according to claim 1, wherein the substance is vaporised in a number of inspiratory cycles.

8. A method according to claim 1, wherein the target temperature is selected such that only constituents in the substance which have a relatively low boiling point are vaporized.

9. A method according to claim 1, wherein the resistive element is a foil.

10. A method according to claim 1, wherein the resistive element is a mesh which is sized so that, in use, the thermal mass of the medicament is sufficient to produce the relatively cool central region.

* * * * *